(12) United States Patent
Gasporra

(10) Patent No.: US 7,066,735 B1
(45) Date of Patent: Jun. 27, 2006

(54) MOUTH BLOCK

(76) Inventor: Andrea R. Gasporra, 2231 Kelmscott Ct., Westlake Village, CA (US) 91361

(*) Notice: Subject to any disclaimer, the term of this patent is extended or adjusted under 35 U.S.C. 154(b) by 0 days.

(21) Appl. No.: 11/179,444

(22) Filed: Jul. 11, 2005

(51) Int. Cl.
*A61C 5/00* (2006.01)
(52) U.S. Cl. .................................................. 433/140
(58) Field of Classification Search ........... 433/140, 433/1, 93, 2, 29, 138, 136; 600/238; 128/862; 24/17, 18, 30.5 R, 30.5 P, 30.5 W
See application file for complete search history.

(56) References Cited

U.S. PATENT DOCUMENTS

| RE20,389 E | * | 6/1937 | Pickett | 600/238 |
| 2,220,674 A | * | 11/1940 | Bloomheart | 600/238 |
| 4,372,314 A | * | 2/1983 | Wall | 604/367 |
| 4,869,669 A | * | 9/1989 | Grubbs | 433/140 |
| 5,033,462 A | * | 7/1991 | Storey et al. | 602/79 |
| 5,588,836 A | * | 12/1996 | Landis et al. | 433/93 |
| 5,673,829 A | * | 10/1997 | Hartshorn | 224/256 |
| 6,030,217 A | * | 2/2000 | Fletcher | 433/140 |
| D442,851 S | * | 5/2001 | Wilson | D8/394 |
| 6,244,866 B1 | * | 6/2001 | Campbell | 433/140 |
| 6,449,808 B1 | * | 9/2002 | Zappa et al. | 24/16 PB |
| 6,634,884 B1 | * | 10/2003 | Phillips | 433/138 |
| 6,640,393 B1 | * | 11/2003 | Wendle | 24/16 PB |

* cited by examiner

*Primary Examiner*—Todd E. Manahan
*Assistant Examiner*—Meoghan E. MacPherson
(74) *Attorney, Agent, or Firm*—Jack C. Munro

(57) ABSTRACT

A mouth block formed of either cotton, plastic or rubber which is to be placed between the teeth of a mandible and the teeth of a maxilla of a jaw to prevent chewing action. The mouth block has a tapered configuration with the widest part of the taper to be located near the front teeth and the narrowest part of the taper to be located directly adjacent the back teeth. The mouth block my include an attachment that facilitates the connection to a lanyard or a rod for the purpose of removing of the block when such is desired.

2 Claims, 2 Drawing Sheets

MOUTH BLOCK

BACKGROUND OF THE INVENTION

1. Field of the Invention

The subject matter of this invention is directed to dental equipment and more particularly to a mouth block that is to be used by dentists and dental specialists to prop open the patient's mouth to prevent chewing action during the time that the patient is recovering from a local anesthetic.

2. Description of the Related Art

Dentists and dental specialists commonly inject local anesthetic into the gum area when performing dental procedures. This local anesthetic will numb a significant area of the cheek and the tongue as well as the surrounding tissue. After the dentist or dental specialist has completed the procedure on the patient, it is desirable to not have the patient perform any chewing action. The dentist and dental specialist would prefer the chewing action be terminated for a period of time until the anesthetic wears off. This recovery time normally is one to two hours in duration. If the patient does perform a chewing action, the patient can frequently injure himself or herself in biting the tongue or the cheek.

In the past, in order to prevent this chewing action it has been common for dentists and dental specialists to take cotton squares or rolls and insert it within the patient's mouth. The patient is to keep the cotton squares or roll between their teeth for a desired period of time at which point the patient will remove it and discard such. This means that after the patient has left the dentist or dental specialist's office and is out in public, the appearance of the cotton in one's mouth is not exceedingly attractive. Additionally, the cotton becomes impregnated with saliva and frequently becomes crushed to the point to where the patient can almost perform a chewing action even with the cotton in place.

It would be desirable to design some type of device that was specifically intended to hold apart the teeth of the mandible from the teeth of the maxilla to prevent a patient from chewing where this device could be reasonably attractive and would not deteriorate in a period of a couple of hours during the time that it is required to be used.

SUMMARY OF THE INVENTION

The first basic embodiment of the present invention comprises a mouth block that is to be constructed of cotton which has an outer end and an inner free end. The body is tapered from the inner free end to the outer end with the widest part of the body being at the outer end. An attachment is mounted at the outer end. Whereby the body is to be placed within the mouth and to be located between the teeth of the mandible and the teeth of the maxilla to prevent chewing action. A lanyard is to be connected to the attachment. The lanyard is to facilitate manual removing of the body when removal is desired.

A further embodiment of the present invention is where the first basic embodiment is modified by defining that the attachment comprises a string loop.

A further embodiment of the present invention is where the first basic embodiment is modified by defining that the cotton body of the mouth block in transverse cross-section is rectangular.

A second basic embodiment of the present invention is directed to a rubber or plastic structure having a first outer end and first inner free end. The body is tapered from the first inner free end to the first outer end with the widest part of the body being at the first outer end. An attachment is mounted within the body located directly adjacent the first outer end. An elongated flexible member is attached to the first outer end. This elongated flexible member is to connect with the attachment forming a loop. The body is to be placed within a mouth and to be located between the teeth of a mandible and the teeth of a maxilla to prevent chewing action. The loop is to be manually used to facilitate removal of the body when such is desired.

A further embodiment of the present invention is where the second basic embodiment is modified by defining that the attachment comprises a through hole.

A further embodiment of the present invention is where the second basic embodiment is modified by defining that the elongated flexible member comprises a rod.

A further embodiment of the present invention is where the second basic embodiment is modified by defining that the second outer end includes an annular protuberance with this annular protuberance to produce a snap fit with the hole to permanently secure the rod to the body.

A further embodiment of the present invention is where the second basic embodiment is modified by defining that the exterior surface of the body includes a plurality of sawtooth sections which is to come into contact with the teeth.

A third basic embodiment of the present invention comprises a mouth block comprising a body constructed of a rubber or plastic and having an outer end and an inner free end, the body having a tapered wall surface that extends from the inner free end to the outer end. The widest part of the body is at the outer end. A through hole is formed in the body located directly adjacent the outer end. The through hole is adapted to be used by a dentist or dental specialist to connect a length of dental floss or similar string.

A further embodiment of the present invention is where the third basic embodiment is modified by the tapered wall surface having texturing.

A further embodiment of the present invention is where the just previous embodiment is modified by defining the texturing as a plurality of sawtooth sections.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figures 1, 2:
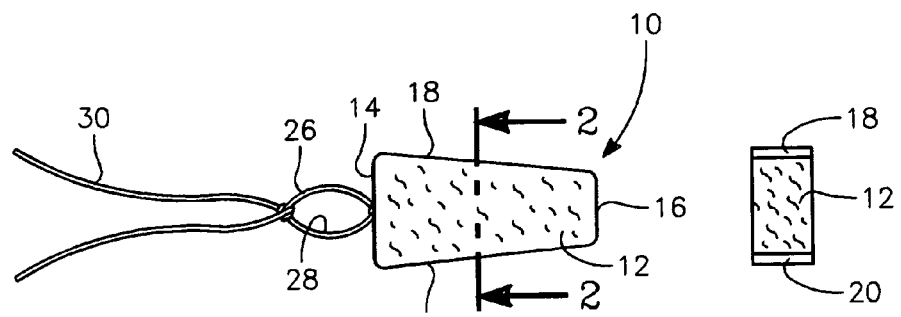
FIG. 1 is a right side view of the first embodiment of mouth block of the present invention with the left side view being identical.
FIG. 2 is a transverse cross-sectional view taken along line 2—2 of FIG. 1.
Figure 3:
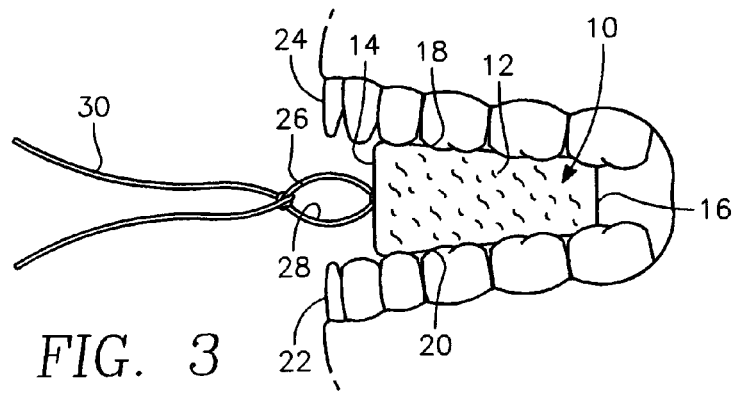
FIG. 3 is a view similar to FIG. 1 but showing the mouth block of the present invention inserted between the teeth of the mandible and the teeth of the maxilla within a patient's mouth.
Figures 4, 5:
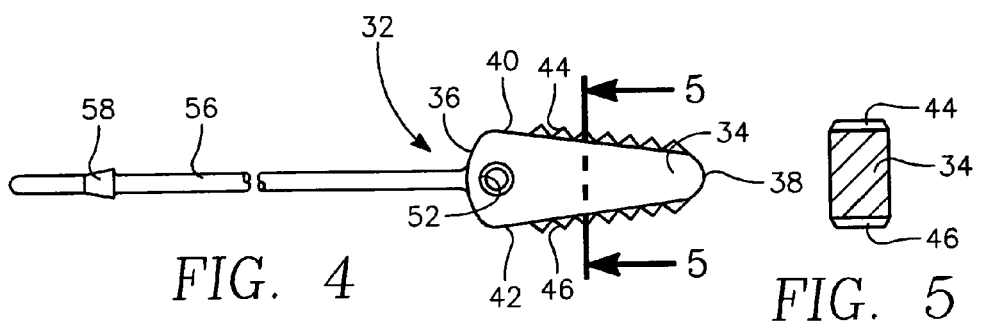
FIG. 4 is a right side view of the second embodiment of mouth block of the present invention which is to be constructed of either rubber or plastic.
FIG. 5 is a transverse cross-sectional view taken along line 5—5 of FIG. 4.
Figure 6:
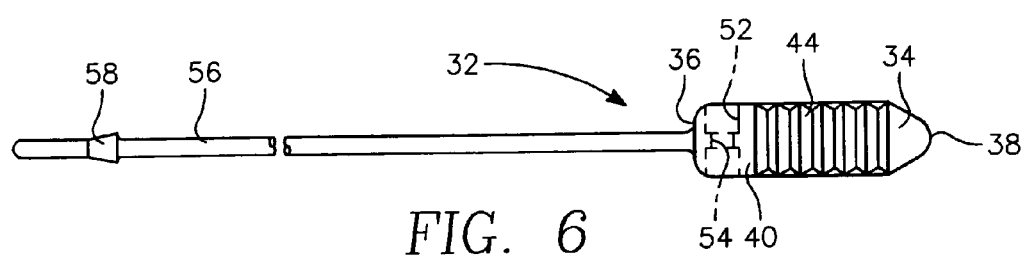
FIG. 6 is a top plan view of the second embodiment of mouth block of the present invention.
Figure 7:
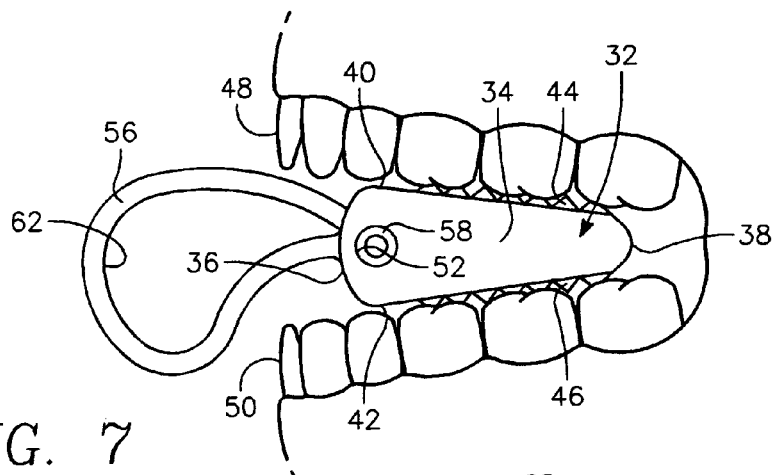
FIG. 7 is a view similar to FIG. 4 but showing the mouth block installed between the mandibular teeth and the maxillary teeth within a patient's mouth and also to where the elongated flexible member that is attached to the mouth block is connected with the attachment of the mouth block forming a loop.
Figures 8, 9:
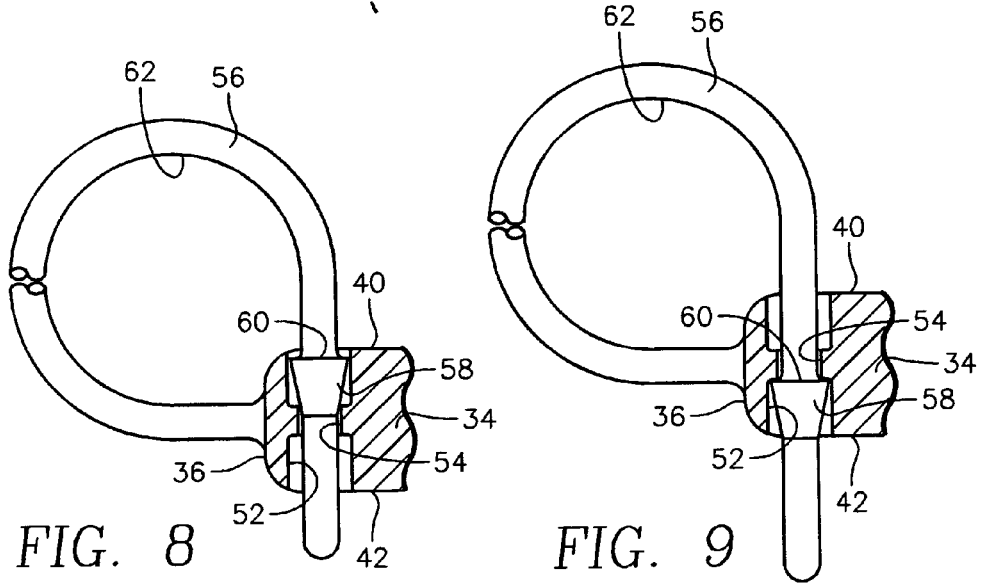
FIG. 8 is a view partly in cross-section showing the installation procedure for the elongated flexible member in conjunction with the attachment hole formed within the mouth block of the present invention.
FIG. 9 is a view similar to FIG. 8 but showing the elongated flexible member completely installed in conjunction with the mouth block.

Referring particularly to the drawings, there is shown in FIGS. 1–3 the first embodiment 10 of mouth block of this invention. Mouth block 10 is formed of a cotton body 12 in the shape of a block. The cotton body 12 has an inner free end 16 and a first outer end 14. The body 12 is basically rectangular in transverse cross-section and defines an upper surface 18 and a lower surface 20. The basic overall configuration of the body 12 is that it is tapered from the inner free end 16 to the first outer end 14. This tapering is such that the widest dimension of the body 12 is located at the first outer end 14. The reason for this is that when the body 12 is placed between the mandibular teeth 22 and the maxillary teeth 24 and because of the hinge-like motion of the jaw, the mouth opening will be wider at the front of the mouth than at the rear of the mouth and the tapering of the body 12 is to essentially duplicate the opening that is produced between the mandibular teeth 22 and the maxillary teeth 24. This is clearly shown in FIG. 3. The mandibular teeth 22 are to be pressed against the lower surface 20 and the maxillary teeth 24 are to be pressed against the upper surface 18. Since the body 12 of this invention is constructed of tightly bound cotton, the teeth 22 and 24 will have a certain resilient action against the body 12. It is not desired that the body 12 be constructed of a hard material and that it would have a certain resiliency.

Secured to the first outer end 14 is an attachment in the form of a string loop 26. The string loop 26 could be embedded within the body 12 at the first outer end 14. The normal size of the string loop 26 would normally produce about an opening 28 within the string loop about one-half inch in diameter. A lanyard 30, which would normally comprise about a ten inch or greater length of string, is to be secured to the string loop 26.

The dentist or dental specialist, prior to installation of the first embodiment 10 of this invention in between the mandibular teeth 22 and the maxillary teeth 24 of the patient, will install the lanyard 30 in position on the string loop 26. The purpose of the lanyard 30 is that after the body 12 has been installed a short period of time, such as one to two hours and the anesthetic has worn off to which the patient had been subjected, the patient can than grab onto the lanyard 30 and pull the body 12 out of the mouth of the patient and discard such.

Referring particularly to FIGS. 4–9 of the drawings, there is shown the second embodiment 32 of mouth block of the present invention. The second embodiment 32 defines a basically tapered shaped body 34 which is to be typically constructed of a plastic or rubber material. The body 34 has an inner free end 38 and an outer end 36. The body 34 has an upper surface 40 and a lower surface 42. Formed within the upper surface 40 is a sawtooth section 44. Formed within the lower section 42 is a sawtooth section 46. Sawtooth sections 44 and 46 are to be considered a form of a textured surface and other hiatused surfaces could be used. Flat surfaces could also be substituted for the sawtooth sections 44 and 46. The sawtooth section 44 is adapted to be located against the maxillary teeth 48 of the jaw, while the sawtooth section 46 is adapted to be located against the mandibular teeth 50 of the jaw. Again, the general tapering configuration of the body 34 of the second embodiment 32 is to essentially duplicate the configuration of the opening between the maxillary teeth 48 and the mandibular teeth 50.

Formed through the body 34 directly adjacent the second outer end 36 is a hole 52. The wall of the hole 52 includes an inwardly extending protrusion 54. The protrusion 54 is basically annular. Fixedly secured to the outer end 36 is an elongated flexible member 56 which is again basically constructed of rubber or plastic. Typically, this elongated flexible member 56 will be six to ten inches in length. Near the outer end of this elongated flexible member 56 is located an annular protrusion 58. This annular protrusion 58 has an exterior configuration and is basically in the shape of a truncated cone. At the widest diameter portion of the protrusion 58 there is formed a shoulder 60 which extends from the elongated flexible member 56.

The dentist or dental specialist prior to installation of the second embodiment 32 in position within the mouth of the patient, will grasp the elongated flexible member 56 and insert the outer end of such into hole 52. This insertion is to be sufficient until the shoulder 60 passes beyond the protrusion 54 and upon doing such will be snappingly installed in place not permitting withdrawal of the elongated flexible 56 member as it is now permanently installed. The elongated flexible member 56 now forms a loop 62. The loop 62 can be used to insert a user's finger there within and exert a pulling action on the elongated flexible member to withdraw the second embodiment 32 of mouth block of this invention after the local anesthetic has worn off. After the second embodiment 32 has been removed from the patient's mouth, the second embodiment 32 is to be discarded.

Figures 10, 11, 12:
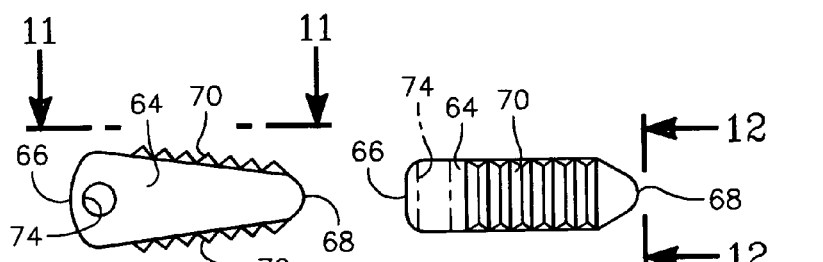
FIG. 10 is a side elevational view of a modified form of the present invention where the body does not include any elongated flexible member.
FIG. 11 is a top plan view of the present invention taken along line 11—11 of FIG. 10.
FIG. 12 is an end elevational view of the present invention taken along line 12—12 of FIG. 11.

In a further embodiment of the present invention, which is shown in FIGS. 10–12, there is a structure of body 64 which has a tapered sidewall that extends from an outer end 66 and an inner free end 68. A tapered sidewall of the body 64 that extends from outer end 66 to inner free end 68 is to be textured by including sawtooth sections 70 and 72. However, it is considered to be within the scope of this invention that the tapered sidewall could be flat. Formed within the body 64 directly adjacent the outer end 66 is a through hole 74. The wall surface of the through hole 74 is smoothly contoured and basically cylindrical, as is clearly shown in FIG. 11. There is no need for the annular protrusion 54. The user can attach their own lanyard in the form of a length of dental floss (or similar string) to the body 64 by using hole 74. This string is not shown.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative of a broader function or of a great variety of alternative or equivalent elements.

Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A mouth block comprising:

a body constructed from a group consisting of rubber and plastic, said body having a first outer end and an inner free end, such body being tapered from said inner free end to said first outer end with the widest part of said body being at said first outer end;

a round hole formed within said body located directly adjacent said first outer end, said round hole having an inwardly extending annular protrusion; and an elongated flexible rod attached to said first outer end, said rod having a second outer end, a truncated cone shaped protrusion mounted on said rod directly adjacent said second outer end, said elongated flexible member rod to connect with said hole forming a loop by said truncated cone shaped protrusion snap fittingly connecting with said inwardly extending annular protrusion, said body is to be placed within a mouth and to be located between the teeth of a mandible and the teeth of a maxilla to prevent chewing action, said loop to be manually used to facilitate removal of said body when removal is desired.

2. The mouth block as defined in claim 1 wherein:

said body having an exterior surface which is formed partially into a pair of sawtooth sections, said sawtooth sections to be located against the teeth.

* * * * *